(12) United States Patent
Marillonnet

(10) Patent No.: US 11,254,929 B2
(45) Date of Patent: Feb. 22, 2022

(54) METHOD, SUBSTRATE AND KIT FOR ONE-POT ONE-STEP ASSEMBLY OF DNA MOLECULES

(71) Applicant: Leibnitz-Institut fuer Pflanzenbiochemie (IPB), Halle (DE)

(72) Inventor: Sylvestre Marillonnet, Halle (DE)

(73) Assignee: Leibniz-Institut fuer Pflanzenbiochemie (IPB), Halle (DE)

( * ) Notice: Subject to any disclaimer, the term of this patent is extended or adjusted under 35 U.S.C. 154(b) by 328 days.

(21) Appl. No.: 16/071,822

(22) PCT Filed: Feb. 1, 2017

(86) PCT No.: PCT/DE2017/200014
§ 371 (c)(1),
(2) Date: Jul. 20, 2018

(87) PCT Pub. No.: WO2017/133738
PCT Pub. Date: Aug. 10, 2017

(65) Prior Publication Data
US 2019/0032040 A1    Jan. 31, 2019

(30) Foreign Application Priority Data
Feb. 4, 2016  (DE) .................. 10 2016 101 948.8

(51) Int. Cl.
*C12N 15/00*   (2006.01)
*C12N 15/10*   (2006.01)
*C12Q 1/6806*  (2018.01)
*C12N 15/66*   (2006.01)

(52) U.S. Cl.
CPC ....... *C12N 15/102* (2013.01); *C12N 15/1006* (2013.01); *C12N 15/66* (2013.01); *C12Q 1/6806* (2013.01); *C12Q 2521/101* (2013.01); *C12Q 2521/501* (2013.01)

(58) Field of Classification Search
CPC ...... C12N 15/10; C12N 15/66; C12N 15/102; C12N 15/1006; C12Q 1/6806; C12Q 2521/101; C12Q 2521/501
See application file for complete search history.

(56) References Cited

U.S. PATENT DOCUMENTS

2002/0025561 A1* 2/2002 Hodgson ............... C12N 15/66
                                                         435/91.1
2013/0280695 A1  10/2013 Hillebrand et al.

FOREIGN PATENT DOCUMENTS

| WO | 9003959 A1 | 4/1990 | |
| WO | 2012010708 A1 | 1/2012 | |
| WO | WO-2012010708 A1 * | 1/2012 | .......... C12Q 1/6834 |
| WO | 2014004393 A1 | 1/2014 | |
| WO | 2015011203 A1 | 1/2015 | |
| WO | WO-2015011203 A1 * | 1/2015 | ......... C12N 15/1006 |
| WO | 2015057330 A1 | 4/2015 | |

OTHER PUBLICATIONS

Engler et al., (2008, PLoS ONE 3 (e3647):1-7; IDS reference). (Year: 2008).*
Engler et al., (2009, PLoS ONE 4 (e5553):1-9; IDS reference). (Year: 2009).*
International Search Report dated Jun. 1, 2017, in International Application No. PCT/DE2017/200014.
Ernst Weber et al: "A Modular Cloning System for Standardized Assembly of Multigene Constructs", PLOS ONE, vol. 6, No. 2, Feb. 18, 2011 (Feb. 18, 2011), p. e16765, XP055110994, ISSN: 1932-6203, DOI: 10.1371/journal.pone.0016765 cited in the application the whole document.
Engler C et al: "A one pot, one step, precision cloning method with high throughput capability", PLOS ONE, Public Library of Science, US, vol. 3, No. 11, Nov. 5, 2008 (Nov. 5, 2008), p. E3647-1, XP002613221, ISSN: 1932-6203, Doi: 10.1371/JOURNAL.PONE.0003647 the whole document.
Siying Ma et al: "DNA synthesis, assembly and applications in synthetic biology", Current Opinion in Chemical Biology, vol. 16, No. 3-4, Aug. 1, 2012 (Aug. 1, 2012), pp. 260-267, XP055212288, ISSN: 1367-5931, DOI: 10.1016/j.cbpa.2012.05.001 the whole document.
Nicola J Patron et al: "Standards for plant synthetic biology: a common syntax for exchange of DNA parts", New Phytologist, Oct. 1, 2015 (Oct. 1, 2015), pp. 13-19, XP055372645, England DOI: 10.1111/nph.13532, Retrieved from the Internet: URL:http://onlinelibrary.wiley.com/store/10.1111/nph.13532/asset/nph13532.pdf?v=1&t=j2pwv4kj&s=79c87eb366c615bda39b895b70e264395f9a2dd1 the whole document.
Sylvestre Marillonnet et al: "Assembly of Multigene Constructs Using Golden Gate Cloning" Glyco-Engineering; Methods and Protocols, Methods in Molecular Biology, vol. 1321, pp. 269-284, DOI 10.1007/978-1-4939-2760-9_19, Springer Science+Business Media New York 2015.
Siying Ma et al: "DNA Synthesis, Assembly and Applications in Synthetic Biology" NIH Public Access, Curr Opin Chem Biol. Aug. 2012; 16(3-4); 260-267. doi:10.1016/j.cbpa.2012.05.001.

(Continued)

*Primary Examiner* — Catherine S Hibbert
(74) *Attorney, Agent, or Firm* — Patent Central LLC; Stephan A. Pendorf

(57) ABSTRACT

A method for one-pot one-step assembly of two or more DNA molecules to form at least one recombinant DNA molecule, and a substrate and a kit for this purpose. A simple and cost-effective assembly method for DNA molecules. A method for one-pot one-step assembly of two or more DNA molecules to form at least one recombinant DNA molecule is provided, wherein the two or more DNA molecules to be assembled are brought together in dry form with a suitable reaction medium on at least one substrate present in a reaction vessel.

8 Claims, 3 Drawing Sheets
Specification includes a Sequence Listing.

(56) References Cited

OTHER PUBLICATIONS

International Preliminary Report on Patentability dated Aug. 7, 2018, issued in International Application No. PCT/DE2017/200014.

Icasini, Arturo et al. "Bricks and blueprints: methods and standards for DNA assembly" Nature Reviews Molecular Cell Biology, Advance Online Publication, published online Jun. 17, 2015; doi: 101.1038/nrm4014.

Brueckner, Kathleen et al. "A library of synthetic transcription actdivator-like effector-activated promoters for coordinated orthogonal gene expression in plants" The Plant Journal (2015), vol. 82, pp. 707-718, doi: 10.1111/tpj.12843.

Gibson, Daniel G. et al. "Enzymatic assembly of DNA molecules up to several hundred kilobases" Nature Methods, vol. 6, No. 5, May 2009, pp. 343-345, published online Apr. 12, 2009; DOI:10.1038/NMETH.1318.

Patron, Nicola J. et al. "Standards for plant synthetic biology: a common syntax for exchange of DNA parts" New Phytologist (2015), vol. 208, pp. 13-19, www.newphytologist.com.

Smith, LM et al. "Collecting, archiving and processing DNA from wildlife samples using FTA databasing paper" BMC Ecology 2004, 4:4, published Apr. 8, 2004, pp. 1-11.

\* cited by examiner

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: pICH50251 section

<400> SEQUENCE: 1
ttaatgggag acctt                                                        15

<210> SEQ ID NO 2
<211> LENGTH: 15
<212> TYPE: DNA
<213> ORGANISM: Artificial Sequence
<220> FEATURE:
<223> OTHER INFORMATION: pICH50251 section

<400> SEQUENCE: 2
aaggtctcag cttac                                                        15

<210> SEQ ID NO 3
<211> LENGTH: 15
<212> TYPE: DNA
<213> ORGANISM: Artificial Sequence
<220> FEATURE:
<223> OTHER INFORMATION: pAGM6752 section

<400> SEQUENCE: 3
gtggtctcaa atggc                                                        15

<210> SEQ ID NO 4
<211> LENGTH: 15
<212> TYPE: DNA
<213> ORGANISM: Artificial Sequence
<220> FEATURE:
<223> OTHER INFORMATION: pAGM6752 section

<400> SEQUENCE: 4
gagctttgag accac                                                        15

<210> SEQ ID NO 5
```

```
<211> LENGTH: 15
<212> TYPE: DNA
<213> ORGANISM: Artificial Sequence
<220> FEATURE:
<223> OTHER INFORMATION: pICH47732 section

<400> SEQUENCE: 5
ccggagtgag accgc                                                      15

<210> SEQ ID NO 6
<211> LENGTH: 15
<212> TYPE: DNA
<213> ORGANISM: Artificial Sequence
<220> FEATURE:
<223> OTHER INFORMATION: pICH47732 section

<400> SEQUENCE: 6
acggtctcac gctgc                                                      15

<210> SEQ ID NO 7
<211> LENGTH: 15
<212> TYPE: DNA
<213> ORGANISM: Artificial Sequence
<220> FEATURE:
<223> OTHER INFORMATION: pICH42301 section

<400> SEQUENCE: 7
gtggtctcag gagag                                                      15

<210> SEQ ID NO 8
<211> LENGTH: 15
<212> TYPE: DNA
<213> ORGANISM: Artificial Sequence
<220> FEATURE:
<223> OTHER INFORMATION: pICH42301 section

<400> SEQUENCE: 8
gacgcttgag accac                                                      15
```

METHOD, SUBSTRATE AND KIT FOR ONE-POT ONE-STEP ASSEMBLY OF DNA MOLECULES

BACKGROUND OF THE INVENTION

Field of the Invention

The invention relates to a method for one-pot one-step assembly of two or more DNA molecules to form at least one recombinant DNA molecule, and a substrate and a kit for this purpose.

Description of the Related Art

The objective of synthetic biology is to engineer living organisms with new phenotypes which do not exist in nature. Efficient methods for the joining together of DNA fragments which are necessary in order to create multigene constructs constitute fundamental tools for synthetic biology. A number of suitable methods for the recombination have been developed in recent years, including the "Gibson Assembly" method (Gibson et al. 2009, Nature Methods 6, 343-345) and "Golden Gate Cloning" (Engler et al. 2008, Plos ONE 3 (11): e3647, doi:10.1371/journal-.pone.0003647). Both methods allow the joining together of multiple DNA fragments in a one-pot one-step reaction with extremely high efficiency. With both methods most colonies contain the anticipated construct following a transformation of the recombination reaction in competent E.-coli cells.

Although the availability of efficient DNA recombination methods can facilitate the joining together of DNA constructs, the provision of a cloning strategy is still a limiting factor. Large multigene constructs require the development of successive cloning steps in order to generate step-for-step larger constructs with more genes. At some point, large constructs will highly likely contain multiple restriction sites for a multitude of restriction enzymes, which may rule out their use for the insertion of further genes into the construct and makes the development of a cloning strategy increasingly difficult. The use of standardisation principles in systems of this kind might afford a solution to this problem. Standardisation of parts consists of a definition of standard structures for constructs that contain the sequences for fundamental genetic elements, such as promoters, encoding sequences, and terminators. Such biological standard parts (building blocks) are flanked by restriction sites. Restriction enzymes for these positions are then used for the joining together of these DNA fragments, for example so as to generate transcription units. Some restriction sites can also be deliberately eliminated from internal sequences of the base modules so as to enable the use of the enzymes in question for further assembly steps. A number of standard procedures have been proposed which differ in the choice of the restriction sites flanking the base module (Cassini et al. 2015, Nat Rev Mol Cell Biol 16(9) 568-576). The "Modular Cloning (MoClo)" system is an example of a standardised cloning procedure of this kind (Weber et al. 2011, Plos ONE, 6(2): e16765, doi: 10.1371./journal.pone.0016765, Patron et al. 2015, New Phytol., 208, 13-19).

The use of standardised individual parts facilitates the joining together of large constructs, since a universal cloning strategy can be taken which is independent of the nature of the individual parts that are to be newly combined. It also facilitates a recycling of individual parts in many different constructs, since all modules of the same type have the same assembly properties and therefore can be swapped for other parts of the same type. For example, a promoter that is cloned as a standard part can be swapped for any other standard promoter for the assembly of transcription units, and the same assembly procedure can be used.

An additional advantage of standardised modules of this kind is the fact that these individual parts can also be used by scientists in other laboratories using the same standards. It can thus be anticipated that the number of modules of this kind will grow significantly, since parts having the same standards can be constructed and used by many different laboratories. The number of biological modules of this kind that can be generated for the purposes of synthetic biology is in theory unlimited. For example, all encoding and regulatory sequences of any living organism could be cloned and used as standardised biological modules, provided they are cloned using a defined standard. In addition to modules derived from living organisms, synthetic modules that do not exist in nature can also be generated. For example, libraries of synthetic promoters can be created, containing segments of defined sequences and also segments of degenerated sequences (Brückner et al. 2015, Plant J. 82, 707-716).

As soon as basic biological modules have been created, they must be preserved for subsequent use. Such DNA modules are usually stored as purified plasmid DNA in a buffer solution frozen at −20° C. Alternatively, these modules can also be stored as glycerol cultures at −80° C. The glycerol culture contains a bacteria strain that has been transformed with the plasmid DNA containing the standard module. In this case, DNA must be extracted from freshly cultivated E. coli cells prior to use in a new cloning. Since not all the extracted and purified plasmid DNA is usually used in an experiment, the rest is usually frozen at −20° C., as described above, for further use.

There are two problems with the storage of purified plasmid DNA at −20° C. Firstly, the storage of DNA at low temperature, i.e. −20° C., is very costly. Whereas this is still acceptable for a limited number of samples, it would become very costly for a very high number of samples and would require a high number of freezers. A second problem is the deterioration of the DNA quality with increasing storage time, even when stored at −20° C. This can lead to reduced cloning efficiency or even to failure of DNA assembly reaction.

An alternative to the storage of DNA or bacteria strains at −20° C. is the storage thereof in dry form at room temperature. However, for cloning purposes, this DNA must firstly be solubilised beforehand in water or buffer and then transformed in E. coli. A bacterial colony with the transformed plasmid is then cultivated in liquid medium, plasmid DNA is extracted, and lastly the DNA concentration of the plasmid preparation is measured. The DNA can be used subsequently for cloning purposes. These processes are very time-consuming and labour-intensive.

There is still a need to improve assembly and cloning methods, in particular to simplify them and make them more economical. The object of the present invention is therefore to provide a simple and inexpensive assembly method for DNA molecules.

BRIEF SUMMARY OF THE INVENTION

In order to achieve the object, a method for one-pot one-step assembly of two or more DNA molecules to form at least one recombinant DNA molecule is provided in accordance with the invention in a first aspect, wherein the two or more DNA molecules to be assembled, present in dry form on or in at least one substrate, are brought together with a suitable reaction medium in a reaction vessel.

The method according to the invention proposes the use of dry DNA aliquots, which can be stored inexpensively, for one-time use for direct DNA assembly. The invention utilises the stability and the low cost of DNA storage in the dry state at room temperature and does not require any transformation of bacterial cells or the extraction of plasmid DNA prior to the cloning.

The method according to the invention provides the use of DNA that is present in the dry state on or in a suitable substrate, preferably in aliquots in a defined quantity. It is particularly preferred if each aliquot of a dry DNA sample is sufficient for an assembly or cloning reaction. This defined DNA quantity can be applied for example for simple handling to a small piece of filter paper or a cellulose particle, for example a particle of microcrystalline cellulose. The cloning would then be performed for example by adding a first filter paper piece or cellulose particle, for example a particle of microcrystalline cellulose, with for example an insert (coding fragment) into a reaction vessel, followed by the addition of a second filter paper or cellulose particle with a suitable vector. Should the cloning be carried out using the "Golden Gate" system with restriction enzyme and ligase, the addition of restriction ligase buffer, restriction enzyme and ligase would follow. With use of the "Gibson Assembly" method the addition of exonuclease, DNA polymerase and DNA ligase could follow. Of course, the reaction medium can also be placed in a reaction vessel, with the DNA aliquots added subsequently. If all components are present together in the reaction vessel, the dry DNA reverts into a soluble form and can be immediately sliced and ligated, which results in the assembly of the desired product.

A "method for one-pot one-step assembly of two or more DNA molecules" or a "one-pot one-step assembly method" are understood here to mean methods such as the "Golden Gate" or "Gibson Assembly" method, in which the synthesis of the resultant recombinant DNA molecule, for example of a cloning vector, can be carried out in one step and in one reaction vessel. Such methods differ from other standard cloning methods in that DNA-cleaving or DNA-degrading and DNA-ligating or DNA-building processes can be performed in parallel without detriment to the synthesis. For example, the "Golden Gate" method does not require separate steps for restriction digestion and ligation, whereas this is indeed necessary in other standard cloning methods, which arises from the fact that ligated DNA fragments can be newly digested after ligation, since the restriction enzyme sites for the cloning are re-established by the ligation step.

The expression "assembly of two or more DNA molecules" means the in vitro synthesis of two, three, four or also more, preferably different DNA molecules to form a single DNA molecule. For example, a receiver vector can be assembled with DNA molecules that form or contain encoding or regulatory DNA sequences in order to give a coding vector. The expression "two or more DNA molecules" is of course not to be understood here in a limiting manner such that it refers only to the stated number of molecules, for example an individual DNA molecule A and an individual DNA molecule B. Rather, the expression is to be understood insofar as at least one first DNA molecule (for example a receiver vector) is assembled with at least one second DNA molecule, preferably different from the first (for example having an encoding DNA sequence). A DNA molecule that is to be assembled with another DNA molecule also can be contained for example in a larger nucleic acid molecule or construct that can be closed linearly or annularly, for example in a plasmid, from which it is cut out during the course of the reaction and is assembled with the other DNA molecule.

A "suitable reaction medium" is understood here to mean a preferably aqueous liquid medium, in which the dry DNA molecules dissolve and can react with one another under suitable conditions. For example, the medium can be a buffer solution, which optionally contains suitable enzymes, for example DNA ligase and a restriction enzyme of type IIs.

A "micro reaction vessel" is understood here to mean a reaction vessel that holds sample volumes in the region of nanolitres, microlitres and at most a few millilitres, for example from 0.005 to 2 ml, preferably for example from 0.01 ml to 1.5 ml, or from 0.05 to 0.5 ml. For example, such vessels can be those made of plastic, for example polypropylene (PP), with or without a lid. However, the term also includes the wells for example of microtitre plates or the like.

If reference is made here to a "DNA molecule in dry form", this means that the substrate with the DNA molecule located thereon or therein preferably has a minimum water content. For example, in the case of a simple filter paper as substrate, this can mean that the water content corresponds substantially to that which is present in the case of simple storage at room temperature and ambient humidity. In the case for example of a coated substrate, the water content in the surroundings of the DNA molecule, however, can also lie significantly below the ambient moisture. It is also possible to provide a suitable desiccant in or on the substrate or in the surroundings thereof, in order to keep the DNA molecule dry.

By means of the method according to the invention the cloning of more than one insert in a vector can also be carried out with use of dry DNA aliquots in a single step. For example, the assembly of a transcription unit with a promoter, an encoding sequence and a terminator in a selected vector can be carried out by means of four dry DNA samples: one for the receiver vector and three for each of the base units of this transcription unit. All four fragments, which can be present each on separate substrates, for example filter paper pieces or cellulose particles, also at least partially jointly on a substrate, for example filter paper piece or cellulose particle, would be introduced together with buffer and enzymes into a reaction vessel, similarly to the sub-cloning of a fragment as described above. It is indeed particularly preferred for the preparation of a specific recombinant DNA molecule that each of the DNA molecules to be assembled is present in dried form on/in a separate substrate, preferably in a quantity sufficient for the cloning. However, it is also possible in principle that all or some of the DNA molecules are present on/in a first substrate, for example the receiver vector on/in a first substrate and regulatory/encoding DNA molecules on/in a common second substrate. It is also possible to provide just one type of DNA molecule on/in a substrate in order to be able to provide a library of DNA molecules of this kind on/in one substrate or optionally also a plurality of substrates. For example, a number of several, for example 10, 20, 50 or 100, different promoters could be arranged on/in a single substrate or optionally a plurality of substrates. This can be advantageous for example in order to produce a corresponding library of different DNA constructs which differ in respect of the promoter. It is also possible to provide two or more libraries of this kind of different types of DNA molecules so as to be able to produce a variety of different constructs in a simple way.

The method is particularly suitable for carrying out assemblies of standardised DNA molecules. Here, the molecules are DNA molecules that are present in a standardised form, in which they can be used for example directly in a "Golden Gate" or "Gibson Assembly" method. In particular, in the case of standardised DNA molecules of this kind, the junctions, i.e. the ends that are to be ligated, are coordinated with one another such that assembly also of a number of DNA molecules in a one-pot one-step method, for example a "Golden Gate" or "Gibson Assembly" method is made possible.

The molecules are particularly preferably DNA molecules that are suitable and preferably standardised for the "Golden Gate" method. Here, the two or more DNA molecules present on or hi the substrate are preferably each flanked by type IIs restriction endonuclease sites with opposite orientation. Type IIs restriction endonucleases are restriction endonucleases of which the restriction site to one side lies outside its asymmetric non-palindromic recognition sequence. Type IIs restriction endonucleases are known to a person skilled in the art. Examples of type IIs restriction endonucleases include BsaI, BpiI, BsmBI, SapI and FokI. The term "orientation" relates here to the direction from the recognition sequence of the restriction endonuclease on the DNA to the cleavage site arranged therebeyond on one side.

As already mentioned, the DNA molecules can be present on/in the substrate in a larger DNA construct (linear or circular). The cleavage sites of the type IIs restriction endonuclease are preferably oriented in these constructs such that, aftercutting, the DNA molecule is without the flanking recognition sequences. In the case of a receiver vector, the restriction sites for example are oriented such that, at the time of the cleaving reaction catalysed by the restriction endonuclease, a receiver vector arises from the construct, which does not have a recognition sequence for the type IIs restriction endonuclease. The recognition sequences of the type IIs restriction endonuclease, in the case of a receiver vector as one of the DNA molecules to be assembled, therefore lie outside the receiver vector, whereas the cleavage sites are directed towards the receiver vector. In the case of non-vector DNA, for example regulatory or encoding sequences, for example promoters, terminators, etc., the situation is similar, such that the cleavage sites are preferably directed towards the DNA molecule. DNA molecules of this kind are particularly well suited for the "Golden Gate" method.

For example, filter paper is a potential substrate for the DNA. However, other substrates are also possible, for example cellulose particles (cellulose beads) for example beads made of microcrystalline cellulose (MCC). It is only necessary to load the substrate with a defined DNA quantity and to be able to handle the loaded substrate. For example, the DNA could also be dried together with suitable sugar compounds, such as trehalose and/or other additives, such as polyvinyl alcohol, in the form of a tablet. It is also possible for example to load cellulose beads with the DNA and to coat the cellulose beads, for example with trehalose and/or other additives, such as polyvinyl alcohol. Suitable formulations for tablets or coatings are known to a person skilled in the art. The formulation or coating is preferably selected such that it easily dissolves in the reaction medium in order to release the DNA molecule. The substrate can be of any size, but is preferably fainted and dimensioned such that it can be arranged individually as a whole and unchanged in a micro reaction vessel. The substrate can optionally also be marked in a coloured manner for example, in order to enable simple optical differentiation.

In a second aspect, the invention also relates to a substrate for use in a method according to the invention according to the first aspect, comprising at least one DNA molecule present in dry form which can be assembled with another DNA molecule, wherein the substrate with the DNA molecule is formed and dimensioned such that it can be arranged individually as a whole and unchanged in a micro reaction vessel, and wherein the substrate comprises the DNA molecule in a quantity sufficient for an assembly reaction. Examples of a possible substrate are a filter paper piece or a cellulose particle of suitable shape and size, or a tablet of suitable size and composition with the DNA molecule contained therein. It is also possible to produce a mixture of the DNA molecule and for example a sugar, for example trehalose, or another substance or composition which during the drying process forms a matrix comprising the DNA molecule, and to apply the mixture to a substrate, for example filter paper or cellulose bead, and to dry it. It is indeed preferred that only a certain DNA molecule (for example a promoter, a terminator or the like, optionally contained in a DNA construct, for example a plasmid) is present on a substrate. However, it is also possible in principle to provide two or more DNA molecules on a substrate.

The wording in accordance with which the substrate "is formed and dimensioned such that it can be arranged individually as a whole and unchanged in a micro reaction vessel" in particular means that the substrate with the DNA molecule located thereon or therein is sufficiently small and stable to be placed by hand or also by machine, for example by robot, in a micro reaction vessel, for example a 1.5 ml reaction vessel. Examples of suitable substrates are square filter paper pieces with an edge length for example of 0.5×0.5 mm, 1×1 mm, 1.5×1.5 mm or 2×2 mm, or round filter paper pieces or cellulose beads for example with a diameter of 0.5-3, preferably 0.5-2.5, particularly preferably 0.5-2 mm diameter. However, much smaller substrates, for example with an edge length or diameter less than 0.5 mm are also possible in principle.

The wording in accordance with which the substrate "comprises the DNA molecule in a quantity sufficient for an assembly reaction" means in particular that on or (for example in the case of a tablet) in the substrate there is provided, in dry form, a quantity of the particular DNA molecule such that an assembly reaction takes place following dissolution of the DNA molecule in the reaction solution. A sufficient quantity is in particular a quantity sufficient to generate a quantity of recombinant DNA molecule adequate for example for transformation of *E. coli* cells. A sufficient quantity for example can be a quantity of 1-100 or more fmol, for example a quantity of 5, 10, 20, 25, 30 or 40 fmol present on/in the substrate.

In a third aspect the invention also provides a kit for carrying out the method according to the invention, wherein the kit comprises at least one substrate in accordance with the above-described second aspect of the invention. The kit preferably comprises two or more DNA molecules preferably on/in a separate substrate in a quantity sufficient for the assembly.

The DNA molecules are preferably standardised DNA molecules, particularly preferably DNA molecules suitable for the "Golden Gate" method, as described above. However, the kit according to the invention does not have to comprise all DNA molecules necessary for a specific intended assembly. For example, the kit can also contain a set of promoters, but no terminator and/or no vector. The kit can also comprise merely a set of a type of DNA molecules, for example a set of promoters, as already mentioned above.

The kit according to the invention preferably also comprises a) a type IIs restriction endonuclease and a DNA ligase or b) an exonuclease, a DNA polymerase and a DNA ligase. In these preferred embodiments the kit is particularly suitable for carrying out the "Golden Gate" or "Gibson Assembly" method for cloning.

The invention will be described in greater detail hereinafter on the basis of the accompanying figures and exemplary embodiments for illustrative purposes.

DETAILED DESCRIPTION OF THE INVENTION

Figure 1:
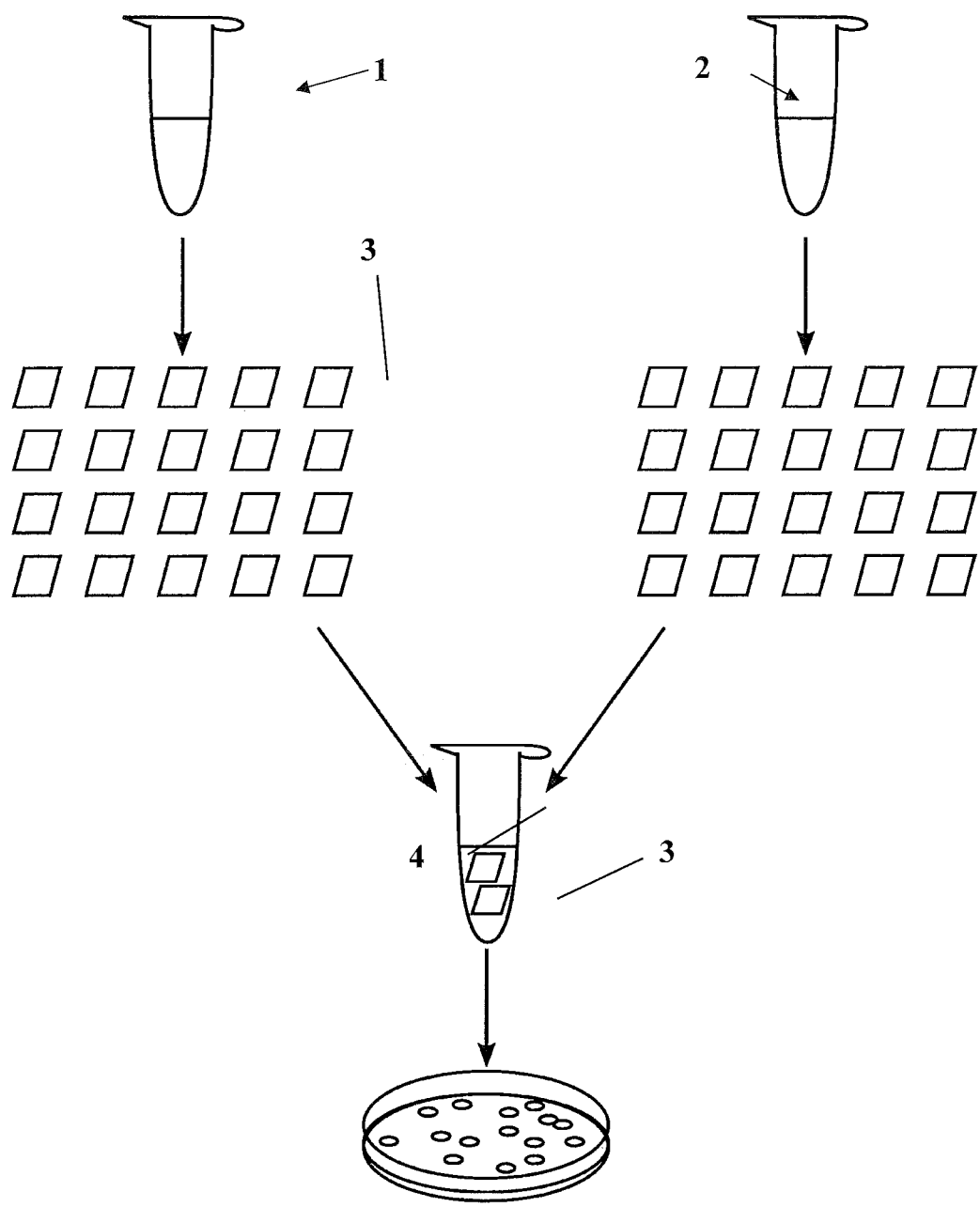
FIG. 1 is a schematic depiction of an embodiment of the method according to the invention.

FIG. 1 shows schematically an embodiment of the method according to the invention. Aliquots of a DNA preparation 1 of the receiver vector and a DNA preparation 2 of an insert are applied in suitable quantity to separate filter paper sheets 3. The filter paper sheets 3 loaded with DNA are dried and stored in a dry environment, for example at room temperature, until use. A filter paper sheet 3 with vector preparation and a filter paper sheet 3 with insert preparation are placed in a reaction vessel 4 and brought into contact with a reaction solution, which for example contains restriction enzyme and ligase. After incubation of the assembly reaction mixture, $E.$ $coli$ for example is transformed with the recombinant plasmid contained in the liquid supernatant.

EXAMPLES

Example 1

Figure 2:
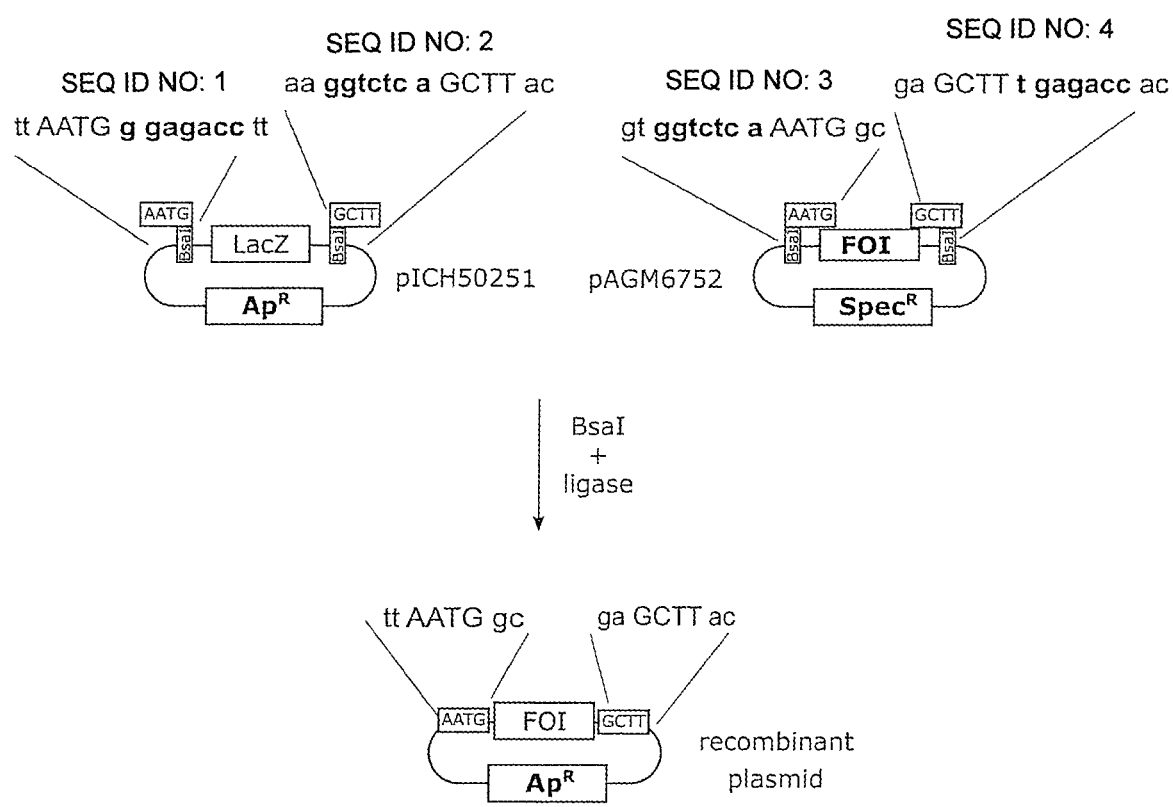
FIG. 2 shows a schematic construction of insert and vector plasmids for use in the embodiment of the method according to the invention depicted in FIG. 1 for the case of "Golden Gate" cloning.

40 fmol (2.4 µL) of plasmid pICH50251 (see left-hand side of FIG. 2 for the construction; depicted sequence portions in SEQ ID NO: 1, 2) were pipetted onto a small piece of filter paper 3 (square with 2 mm edge length), which had been cut out from a larger filter paper (Sartorius, class 6, 80 g/m2 FT 3-312-070). 40 fmol (1.8 µL) plasmid pAGM6752 (see FIG. 2, right-hand sides; depicted sequence portions in SEQ ID NO: 3, 4) were pipetted onto a second filter paper piece 3 of similar size and having similar properties. The two filter paper pieces 3 were then dried at room temperature and stored in the dry state for 24 h.

The two filter paper pieces 3 were placed in a 1.5 mL reaction vessel 4, and 3 µL 10× Promega ligase buffer, 1.5 µL BsaI (15 Units, NEB), 1.5 µL ligase (4.5 Units, Promega) and 24 µL water were added, to give a total reaction volume of 30 µL. The reaction vessel 4 was incubated for 1 h at 37° C., followed by 5 min at 50° C. and 5 min at 80° C.

The total ligation reaction was transformed in 50 µL $E.$ $coli$ DH10b competent cells by means of heat shock. 500 µL of LB liquid medium were added to the cells and incubated for 45 min at 37° C. 50 µL of this transformation batch were plated on selection medium. An approximately equal number of blue and white colonies was obtained (in each case approximately 130 colonies). Four white colonies were picked and cultivated in liquid medium. Plasmid DNA was isolated therefrom, analysed by restriction digestion, and found to be corresponding to the anticipated construct.

This result shows that the cloning can be performed directly from the dried DNA sample applied to a filter paper substrate, without the need to transform the vector and the insert DNA fragment back into bacteria strains for plasmid preparations.

Example 2

Figure 3:
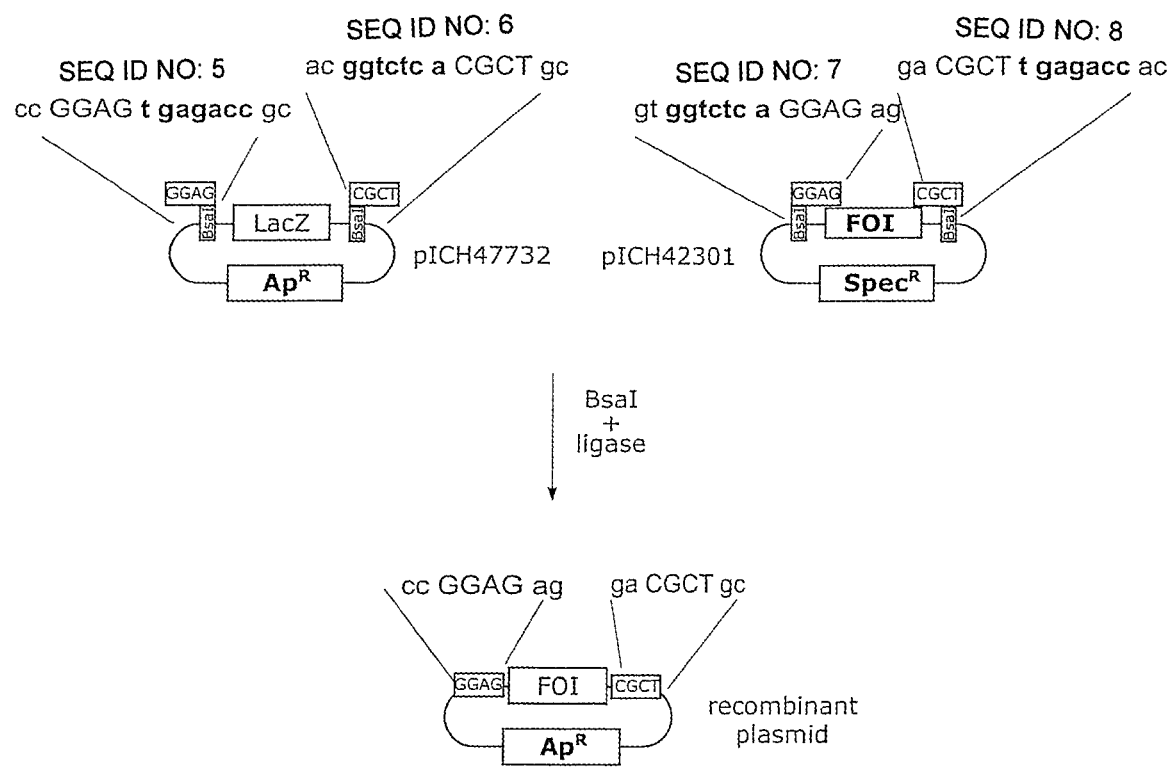
FIG. 3 shows a further schematic construction of insert and vector plasmids for use in the embodiment of the method according to the invention depicted in FIG. 1 in case of a "Golden Gate" cloning.

DNA of the plasmids pICH47732 (insert; equivalent to plasmid pICH50251 in respect of the restriction positions for the "Golden Gate" assembly; construction see left-hand side of FIG. 3; depicted sequence portions in SEQ ID NO: 5, 6) and pICH42301 (vector; equivalent to the plasmid pAGM6752 in respect of the restriction positions for the "Golden Gate" assembly; see right-hand side of FIG. 3; depicted sequence portions in SEQ ID NO: 7, 8) were prepared with use of the Macherey Nagel Miniprep kit "NucleoSpin® Plasmid". The DNA concentrations, which were measured with use of a "NanoDrop" UV-vis spectrophotometer (Thermo Fisher Scientific Inc.), were 275 ng and 172 ng per microlitre, or 89 and 82 fmol per microlitre.

DNA for both plasmids was applied separately to sterile MCC beads, i.e. beads made of microcrystalline cellulose (Cellets® 700, HARKE Pharma GmbH), which were then placed in two separate reaction vessels and were subjected in each case to four separate treatments:

Treatment 1: 10 µL DNA and 10 µL water were added to approximately 55 beads in a 1.5 ml reaction vessel.

Treatment 2: 10 µL DNA and 10 µL of a 5% trehalose solution (sterile) were added to approximately 55 beads in a 1.5 ml reaction vessel.

Treatment 3: 10 µL DNA and 10 µL of a 4% PVA solution (4% polyvinyl alcohol in 200 mM Tris-HCl, pH 8.0; sterile) were added to approximately 55 beads in a 1.5 ml reaction vessel.

Treatment 4: 10 µL DNA and 10 µL of a trehalose-PVA solution (2% trehalose, 4% polyvinyl alcohol, in 200 mM Tris-HCl, pH 8.0; sterile) were added to approximately 55 beads in a 1.5 ml reaction vessel.

DNA and beads of the 8 reaction vessels were air-dried overnight at room temperature. The added DNA quantity for each plasmid should be 15 to 16 fmol per bead.

The next day, a bead coated with pICH47732 and a bead coated with pICH42301 (both from the same treatment) were placed in a common PCR reaction vessel. 12 µL sterile $H_2O$, 1.5 µL 10× ligation buffer, 1 µL ligase and 0.5 µL BsaI restriction enzyme were added to this. The reaction vessel was closed, pinched between the fingers and introduced into a thermocycler with the following parameters 37° C., followed by 5 mM incubation at 50° C. and 5 min at 80° C. The supernatant was transformed by means of heat shock into competent $E.$-$coli$ cells. 30 µL of the 565 µL transformation mixture were plated on LB plates containing X-Gal and Carbenicillin. Plates 1 to 4 had the following colonies:

Treatment 1: 155 white colonies, estimated 23250 for the entire transformation.

Treatment 2: 282 white colonies, estimated 42300 for the entire transformation.

Treatment 3: 196 white colonies, estimated 29400 for the entire transformation.

Treatment 4: 143 white colonies, estimated 21450 for the entire transformation.

For all treatments the majority of the colonies were white and the minority were blue. DNA was extracted from two white colonies per treatment. In all cases it was found that they contained the correct construct.

Cloning with use of MCC beads coated with dry DNA thus proved to be very efficient.

Further experiments were carried out in order to test a longer drying time prior to cloning and to vary the composition of the DNA solution.

DNA for both plasmids was introduced separately to sterile MCC beads (Cellets® 700, HARKE Pharma GmbH) into two separate reaction vessels and was subjected to the following three treatments:

Treatment 5: 10 µL DNA and 10 µL of a 4% PVA solution (4% polyvinyl alcohol in 200 mM Tris-HCl, pH 8.0; sterile) were added to approximately 55 beads in a 1.5 ml reaction vessel (same composition as treatment 3).

Treatment 6: 10 µL DNA, 4 µL of a sterile 4% PVA solution (4% polyvinyl alcohol in 200 mM Tris-HCl, pH 8.0; sterile) and 6 µL water were added to approximately 55 beads in a 1.5 ml reaction vessel.

Treatment 7: 10 µL DNA, 2 µL of a sterile 4% PVA solution (4% polyvinyl alcohol in 200 mM Tris-HCl, pH 8.0; sterile) and 8 µL water were added to approximately 55 beads in a 1.5 ml reaction vessel.

DNA and beads of the 6 reaction vessels were air-dried at room temperature.

Two weeks later, cloning reactions were carried out with a bead of the insert and a bead of the vector, as described beforehand for treatments 1 to 4. The transformation was carried out as described for the previous experiment, resulting in the following number of colonies:

Treatment 5: 250 white colonies, estimated 37500 for the entire transformation.

Treatment 6: 181 white colonies, estimated 27150 for the entire transformation.

Treatment 7: 172 white colonies, estimated 25800 for the entire transformation.

These results show that the beads can be stable for at least 2 weeks at room temperature and are still suitable for efficient cloning.

The invention claimed is:

1. A method for one-pot one-step assembly of two or more DNA molecules to form at least one recombinant DNA molecule, comprising
providing two or more DNA molecules to be assembled, wherein the two or more DNA molecules to be assembled are in dry form on or in at least one substrate selected from the group consisting of a piece of filter paper, a cellulose particle, and a tablet, wherein the two or more DNA molecules are each present on or in the at least one substrate in a quantity sufficient for assembly, and
bringing the two or more DNA molecules to be assembled together with a suitable reaction medium in a reaction vessel such that an assembly of the two or more DNA molecules is brought about.

2. The method according to claim 1, wherein each of the two or more DNA molecules present on or in the substrate is flanked by type IIs restriction endonuclease restriction sites with opposite orientation.

3. The method according to claim 1, wherein the two or more DNA molecules are each present on or in a separate substrate in dried form, and are brought together with the reaction medium in the reaction vessel.

4. The method according to claim 1, wherein the two or more DNA molecules are brought together in a reaction medium which contains a) a type IIs restriction endonuclease and a DNA ligase or b) an exonuclease, a DNA polymerase and a DNA ligase.

5. A kit for use in a method for one-pot one-step assembly of two or more DNA molecules to form at least one recombinant DNA molecule, the kit comprising at least one substrate selected from the group consisting of a piece of filter paper, a cellulose particle, and a tablet, the at least one substrate comprising thereon or therein at least one of the two or more DNA molecules in dry form, which at least one of the two or more DNA molecules can be assembled with the other of the two or more DNA molecules, wherein the at least one substrate with the at least one of the two or more DNA molecules is formed and dimensioned such that it can be arranged individually as a whole and unchanged in a micro reaction vessel, and wherein the at least one substrate comprises the at least one of the two or more DNA molecules in a quantity sufficient for an assembly reaction, and wherein the two or more DNA molecules are flanked in each case by type IIs restriction endonuclease restriction sites with opposite orientation.

6. The kit according to claim 5, wherein each of the two or more DNA molecules is present on or in a separate substrate in a quantity sufficient for the assembly.

7. The kit according to claim 5, further comprising a) a type IIs restriction endonuclease and a DNA ligase or b) an exonuclease, a DNA polymerase and a DNA ligase.

8. A method for one-pot one-step assembly of two or more DNA molecules to form at least one recombinant DNA molecule, comprising:
- (a) providing, in dry form, at least one substrate selected from the group consisting of filter paper, a cellulose particle, and a tablet, having on or in the at least one substrate two or more DNA molecules to be assembled, wherein the two or more DNA molecules are each present on or in the at least one substrate in a quantity sufficient for assembly,
- placing the at least one substrate in a reaction vessel,
- adding a suitable reaction medium to the reaction vessel to provide a reaction mixture of said two or more DNA molecules and said reaction solution, and
- incubating the reaction mixture such that an assembly of the two or more DNA molecules is brought about, or
- (b) providing, in dry form, at least two substrates selected from the group consisting of a piece of filter paper, a cellulose particle, and a tablet, each of the at least two substrates having on or in each substrate at least one of said two or more DNA molecules to be assembled, wherein the two or more DNA molecules are each present on or in the at least two substrates in a quantity sufficient for assembly,
- placing the at least two substrates in a reaction vessel,
- adding a suitable reaction medium to the reaction vessel to provide a reaction mixture of said two or more DNA molecules and said reaction solution, and
- incubating the reaction mixture molecules such that an assembly of the two or more DNA molecules is brought about.

* * * * *